United States Patent [19]

McDermed

[11] Patent Number: 4,681,878
[45] Date of Patent: Jul. 21, 1987

[54] FLUOROPHENO-THIAZINE AND PHARMACEUTICAL USE

[75] Inventor: John D. McDermed, Durham, N.C.

[73] Assignee: Burroughs Wellcome Co., Research Triangle Park, N.C.

[21] Appl. No.: 888,278

[22] Filed: Jul. 23, 1986

Related U.S. Application Data

[63] Continuation of Ser. No. 759,504, Jul. 26, 1985, abandoned, which is a continuation of Ser. No. 678,338, Dec. 5, 1984, abandoned, which is a continuation-in-part of Ser. No. 616,311, Jun. 1, 1984, abandoned.

[51] Int. Cl.$^4$ .................... A61K 31/54; C07D 279/28
[52] U.S. Cl. ........................................ 514/223; 544/41
[58] Field of Search ........................... 544/41; 514/223

[56] References Cited

U.S. PATENT DOCUMENTS 3,112,310 11/1963 Cusic et al. ..................... 544/44

FOREIGN PATENT DOCUMENTS 808239 1/1959 United Kingdom .

OTHER PUBLICATIONS

Gritsenko et al, Chemical Abstracts, vol. 76 (1972), 3774k.

*Primary Examiner*—Richard L. Raymond
*Attorney, Agent, or Firm*—Donald Brown

[57] ABSTRACT

The compound 2-[10-(2-Dimethylaminopropyl)-7-fluoro-2-phenothiazinyl]-2-methylpropionic acid or a pharmaceutically acceptable salt thereof. The compound or salt are useful as antihistamines.

14 Claims, No Drawings

FLUOROPHENO-THIAZINE AND PHARMACEUTICAL USE

This application is a continuation, of application Ser. No. 759,504, filed 7/26/85, now abandoned which is a continuation of Serial No. 678,338 filed Dec. 5, 1984, now abandoned and a continuation in part of Serial No. 616,311 filed June 1, 1984, now abandoned.

The present invention relates to a new chemical compound exhibiting antihistamine and anti-allergic activity, to processes for preparing it, to novel intermediates involved in its preparation, to pharmaceutical compositions containing it and to its use in medicine.

U.S. Pat. No. 2,530,451 discloses a group of 9-(dialkylaminoalkyl)phenothiazines with antihistamine activity, the most outstanding of which is the compound named, and hereinafter referred to by its generic name, promethazine (10-(2-dimethylaminopropyl)phenothiazine). Promethazine has gained a fair degree of clinical acceptance as a tranquillizer and as an antihistamine.

The antihistamines now in use, including diphenylhydramine, the pheniramines, pyrilamine, promethazine and triprolidine have one potential disadvantage in common; they all cause sedation or drowziness in some patients. Promethazine also has the additional disadvantage that it has potent anticholinergic activity.

A novel compound having antiallergic activity in vivo as defined by blockade of anaphylactoid activity has now been discovered, and strong antihistamine activity and appear to be substantially free of CNS side-effects and to possess markedly less anticholinergic activity than promethazine.

Accordingly this invention provides a compound of the formula (I) which has the chemical name 2-[10-(2-dimethylaminopropyl)-7-fluoro-2-phenothiazinyl]-2-methylpropionic acid, or a salt, ester or amide thereof.

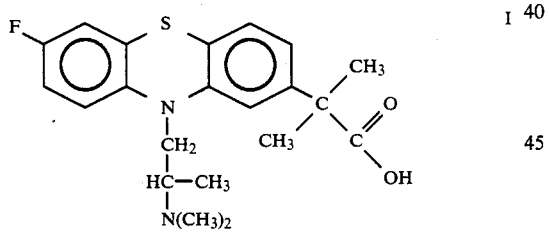

Solvates of the compound of the formula (I) are also included within the scope of the present invention. Preferred solvates include hydrates and $C_{1-4}$ alkanolates.

Esters and amides of the compound of the formula (I) whilst having antihistamine activity in their own right may also be useful intermediates in the preparation of the carboxy compound of the formula (I). Suitable esters include conventional ester groups known to be useful for protecting carboxylic acid group such as $C_{1-6}$ alkyl esters wherein the alkyl group is straight or branched chain and is optionally substituted by halogen. Alkyl esters ($C_{1-4}$) are particularly preferred. Salts of the compound of formula (I) may be either acid addition salts or salts formed with the carboxylic acid group. Acid addition salts are preferred but salts formed from the carboxylic acid group may be particularly useful in preparing the corresponding carboxy compound. Pharmaceutically acceptable salts are preferred.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable acid addition salts include, but are not limited to, those prepared from the following acids: hydrochloric, sulfuric, nitric, phosphoric, maleic, salicyclic, p-toluenesulphonic, tartaric, citric, methanesulphonic, formic, malonic, isothionic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group.

The present invention also provides analogy methods for preparing compounds of formula (I), for example:

(a) A compound of the formula (I) may be prepared by the reaction of a compound of formula (II):

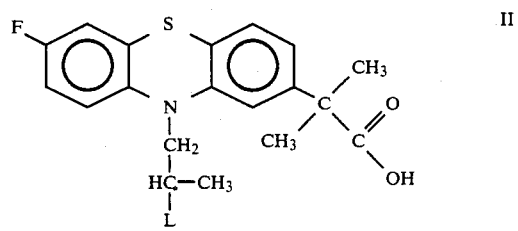

wherein L is a leaving group; or an ester thereof with an amine $HN(CH_3)_2$.

(b) The compound of formula (I) may also be prepared by the oxidation of the corresponding aldehyde (III):

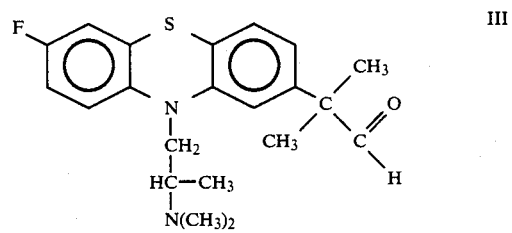

(c) An alternate synthetic route to the compound of formula (I) is the hydrolysis of a compound of formula (IV):

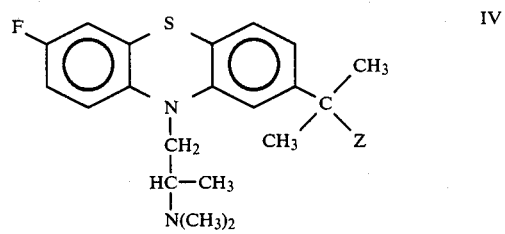

wherein Z is CN, $CONR^1R^1$ or $CO_2R^1$ or $CO_2R^1$ ($R^1$ is $C_{1-4}$ alkyl); or—CH═C(Y) XH X is oxygen or sulphur and Y is a secondary amino group;

(d) The alkylation of a compound for formula (V) may also be used to prepare the company of formula (I):

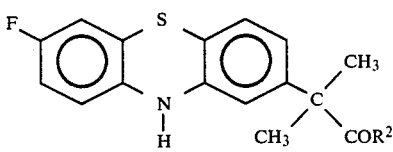

wherein $COR_2$ is an ester or amide group and thereafter, optionally converting the compound of formula (I) to the acid an amide or another salt by methods well known to those skilled in the art.

Suitable leaving group L in the compounds of the formula (III) are those as defined by J. March, *Advanced Organic Chemistry*, 2nd ed., pages 683 and 895, McGraw Hill, New York, 1977, e.g.—Br,—Cl, toluenesulphonate, methanesulphonate, acyloxy (such as acetate), etc.

This reaction will normally be carried out in a solvent suitable for carrying out such displacement reactions, for example a polar solvent, such as a $C_{1-4}$ alkanol or a polar aprotic solvent such as DMSO, at a temperature between 0° and 180° C.

The compounds of the formula (II) may be prepared by the reaction of an ester of the corresponding compound where L is a hydroxy group with an acid or a suitable reactive acid derivative, followed by removal of the ester function if desired. Suitable reactants include hydrogen halides halogenated phosphorus compounds such as phosphorus pentachloride or phosphorus oxychloride, a suitable sulphonyl chloride (such as methanesulphonyl chloride or p-toluenesulphonyl chloride) or an acid anhydride such as acetic anhydride. The reaction will conveniently be carried out in a suitable solvent under conditions well known to those skilled in the art, for example a non-protic solvent such as an ether or a halogenated hydrocarbon, in the presence of a base such as a tertiary amine (for example triethylamine) at a non-extreme temperature, for example between 0° and 100° C. and conveniently at room temperature. When a tertiary amine is used as a base, an excess of this may be used as the solvent. Those intermediates that are novel form an important further aspect of the present invention.

The compound of this invention has antiallergic activity and may be used for the same indications as clinically used antiasthmatic compounds, namely to help to control bronchoconstriction or brochospasm characteristic of allergic asthma and exercise induced asthma and the symptoms of bronchoconstriction and bronchospasm resulting from acute or chronic bronchitis. The compound is believed to inhibit the release of autacoids (i.e. histamine, serotonin and the like) from mast cells and to inhibit directly the antigen-induced production of histamine. Thus, it may be classified as a mast cell stabilizer with antihistaminic action.

The compound of this invention also has strong antihistamine activity and may be used for the same indications as clinically used antihistamines, namely to relieve detrimental symptoms (caused by histamine release) of nasal stuffiness due to colds and vasomotor rhinitis and for the symptomatic control of allergic conditions including nasal allergy, perennial rhinitis, urticaria, angioneurotic oedema, allergic conjunctivitis, food allergy, drug and serum reactions, insect bites and strings and desensitizingreactions. The compound may also be used in conditions responsive to its antipruritic activity including allergic dermatoses, neurodermatitis, anogenital pruritus, and pruritus of nonspecific origin such as eczema, and of specific cause such as chickenpox, photosensitivity and sunburn. The present invention therefore provides a method for the symptomatic treatment of allergic conditions by the administration of an effective amount of the compound of formula (I).

The present invention also provides a method for the antagonism of endogenously released histamine by the administration of an effective amount of the compound of formula (I).

The amount of the compound of formula (I), also referred to as the "active compound", required for use in the above conditions will vary with the compound chosen, the route of administration and the condition and mammal undergoing treatment, and is ultimately at the discretion of the physician. A suitable oral dose of the active compound for a mammal is in the range of from 0.003 to 1.0 mg per kilogram body weight per day; preferably from 0.04 to 0.24 mg/kg. For example a typical dose for a human recipient of compound (B) (see Example 2 and Table 1 hereafter) is between 0.03 and 0.1 mg/kg body weight per day.

The desired daily dose is preferably presented as from one to six subdoses administered at appropriate intervals throughout the day as needed. Where three subdoses of the compound of formula (I) are employed, each will preferably lie in the range of from 0.014 to 0.08 mg/kg body weight; for example, a typical sub-dose of such a compound for a human recipient is between 1 and 20 mg, for example 4 or 8 mg.

Whilst it is possible for a compound of formula (I) to be administered alone as the raw chemical, it is preferable to present the compound of formula (I) as a pharmaceutical formulation. Thus, the present invention also provides pharmaceutical formulations, both for veterinary and for human medical use, which comprise the compound of formula (I) together with one or more pharmaceutically acceptable carriers therefor and optionally any other therapeutic ingredients. For example, the active compound may be formulated with a sympathomimetic agent such as the decongestant pseudoephedrine, an antitussive such as codeine, an analgesic, an antiinflammatory, an antiphretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or nonaqueous liquid such as a syrup, and elixir, an emulsion or a draught. A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol, for example glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to that for the nasal spray except that the pH and isotonic factors are adjusted to match those of the eye.

Topical formulations comprise the active compound dissolved or suspended in one or more media such as mineral oil, petroleum, polyhydroxyl alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like. The present invention also provides the first use of the compounds of formula (I) in medicine.

The following Examples are provided by the way of illustration of the present invention and should in no way be construed as a limitation thereof. All temperatures indicated are in degrees Celsius.

EXAMPLE 1

2-[10-(2-Dimethylaminopropyl)-7-fluoro-2-phenothiazinyl]-2-methylpropionic acid (a) Ethyl 2-methyl-2-3-nitro-4-(4-fluorophenylthio)-phenyl]propionate (Compound ex-17a)

A mixture of Ethyl 2-(4-bromo-3-nitrophenyl)-2-methylpropionate (54.5 g), 4-fluorothiophenol (27 g) and $Na_2CO_3$ (39.2 g) in ethanol (250 mL) was stirred under nitrogen at reflux for 5 hours. It was poured into ice-cold water (1500 mL), stirred well, and the resulting yellow solid was filtered. This solid was dissolved in ether (400 mL), washed with 2%NaOH, and then dried ($MgSO_4$) and evaporated. The product, compound ex-17a, was obtained in quantitative yield as a yellow solid. Its tlc was essentially homogeneous and its nmr spectrum was consistent with the structure indicated. Compound ex-17a was recrystallized from 2-propanol/hexane to give a yellow solid, mp 56°–60° C.

(b) Ethyl 2-methyl-2-(7-fluoro-2-phenothiazinyl)propionate. (Compound ex-17b)

Compound ex-17a (24.3 g) and triethyl phosphite (46.0 g, were combined in dried and deoxygenated n-propylbenzene (200 mL) and refluxed under $N_2$ for 4 hours. The volatile components were removed on the water aspirator at 80° C. The crude product was purified to apparent homogeneity by flash chromatography on silica gel, eluting contaminants with hexane/ethyl acetate (20:1) and then eluting the product with hexane/ethyl acetate (10:1). The product, compound ex-17b, was crystallized from $CH_2Cl_2$/hexane, mp 116°–118° C.

(c) Ethyl 2-[10-(2-dimethylaminopropyl)-7-fluoro-2-phenothiazinyl]-2-methylpropionate. (Compound ex-17c)

Compound ex-17b (4.0 g) and potassium t-butoxide (1.52 g) were combined in dry deoxygenated toluene (30 mL) and stirred under $N_2$ for 10 minutes. 2-chloro-1-dimethylaminopropane (1.7 g) was added, and the reaction was heated at 80° C. for 1 hour. A further 1.5 g potassium t-butoxide and 1.7 g 2-chloro-1-dimethylaminopropane were added and stirring and heating were continued for 2 hours. The reaction was diluted with toluene (50 mL) and washed with water and saturated NaCl. The amines were then extracted into dilute HCl, which was washed once with toluene, basified (litmus, conc $NH_4OH$), and extracted with $CHCl_3$. Evaporation of the $CHCl_3$ yielded the crude product. This product was purified by preparative HPLC using silica gel columns in series. The elution solvents, in sequence, were: hexane/ethyl acetate/ethanol (38:38:3, then 20:20:2.7, then 18:18:3), then changing components to ethyl acetate/ethanol (10:1 and finally 5:1). The free base was a viscous oil from which a crystalline salt was made using HCl/ether and recrystallizing from 2-propanol/ether, giving compound ex-17c hydrochloride, mp 156°–160° C. Elemental, nmr and mass spectral analyses were consistent with the structure indicated.

(d) 2-[10-(2-Dimethylaminopropyl)-7-fluoro-2-phenothiazine]-2-methylpropionic acid.

Compound ex-17c hydrochloride (0.5 g) was suspended in a mixture of 1.0N sodium hydroxide (5.0 mL) and ethanol (5.0 mL). The suspension was heated at reflux for 48 hr and then evaporated to dryness. The residue was dissolved in water (12 mL). The solution was filtered, washed with ether and then acidified with 1.0N hydrochloric acid (7.0 mL). The solution was evaporated to dryness. The residue was digested with 2-propanol (24 mL) and the mixture filtered and evaporated. The residue was recrystallized from methanol/ethyl acetate to give compound 2-[10-(2-Dimethylaminopropyl)-7-fluoro-2-phenothiazinyl]-2-methylpropionic acid hydrochloride, mp 180°–186° C. Elemental analysis, Nmr and mass spectral analyses were consistent with the structure assigned.

2-[10-(2-Dimethylaminopropyl)-7-fluoro-2-phenothiazinyl]-2-methylpropionic acid may be isolated as the free amino acid by carefully neutralizing an aqueous solution of the hydrochloride, thereby precipitating the free amino acid compound 2-[10-(2-Dimethylaminopropyl)-7-fluoro-2-phenothiazinyl]-2-methylpropionic acid.

The sodium salt of 2-[10-(2-Dimethylaminopropyl)-7-fluoro-2-phenothiazinyl]-2-methylpropionic acid may be prepared by adding this compound to a slight molar excess of aqueous sodium hydroxide and then salting out the sodium salt of 2-[10-(2-Dimethylaminopropyl)-7-fluoro-2-phenothiazinyl]-2-methylpropionic acid by adding sodium chloride to the solution. Alternatively, 2-[10-(2-Dimethylaminopropyl)-7-fluoro-2-phenothiazinyl]-2-methylpropionic acid may be added to an aqueous solution of sodium hydroxide containing an equimolar amount of sodium hydroxide and then lyophylizing the solution to give the sodium salt.

EXAMPLE 2

Antihistamine Activity

A. In vitro antihistamine activity: The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., *Br. J. Pharmacol.* 14, 48–58, 1959). Regression of Log (dr-1) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration response curve 2X to the right. The $pA_2$ value found for the compound of formula (I) is 8.6.

B. In vivo Antihistaminic Activity: Guinea pigs (Hartley, male, 300–350 g) were fasted for 20 hours and then dosed p.o. or i.p. with the test compound. One hour after dosing, on an individual basis, the guinea pigs were placed in a clear plastic chamber which was saturated and continually gassed with 0.25% histamine from an aerosol nebulizer. The guinea pigs were monitored for signs of histamine anaphylaxis (e.g. cough, sneeze, strong abdominal movements, cyanoses or loss of righting). Under the test conditions, control animals collapsed on average within 33 seconds. $ED_{50}$'s for protection against histamine were calculated by probit analysis.

In this test the $ED_{50}$ indicates that at that particular dose 50% of the animals were completely protected against histamine challenge at the time of testing (1 hour post-dosing). Complete protection was defined as no histamine symptoms for six minutes in the aerosol chamber (approximately 10X the collapse time of the control animals). The $ED_{50}$ for the compound of formula (I) was found to be $0.04 \leq 1$ mg/kg p.o. and a duration of action from 4 to 30 hrs.

EXAMPLE 3

Formulations

| (A)-Injection | |
|---|---|
| Ingredient | Amount per ampoule |
| Compound of formula (I) | 1.0 mg |
| Water for injections, q.s. | 1.0 mL |

The finely ground active compound was dissolved in the water for injections. The solution was filtered and sterilized autoclaving.

| (B)-Suppository | |
|---|---|
| Ingredient | Amount per suppository |
| Compound of Formula (I) | 1.0 mg |
| Cocoa Butter or Wecobee ™ Base | q.s. to 2.0 g |

Wecobee is a trademark and is a hydrogenated fatty carboxylic acid.

The finely ground active compound was mixed with the melted suppository base (either Cocoa Butter or Wecobee ™ base), poured into moulds and allowed to cool to afford the desired suppositories.

| (C)-Syrup | |
|---|---|
| Ingredient | Amount per mL |
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Colouring | q.s. |
| Water | q.s. to 5.0 mL |

Ethanol, sucrose, sodium benzoate, methylparaben, and flavouring were combined in 70% of the total batch quantity of water. Colouring and the active compound were dissolved in the remaining water, then the two solutions were mixed and clarified by filtration.

| (D)-Tablet | |
|---|---|
| Ingredient | Amount per Tablet |
| Compound of Formula (I) | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound was finely ground and intimately mixed with the powdered excipients lactose, corn starch, potato starch and magnesium stearate. The formulation was then compressed to afford a tablet weighing 126 mg.

| (E)-Capsule | |
|---|---|
| Ingredient | Amount per Capsule |
| Compound of Formula (I) | 1.0 mg |
| Lactose | 440.0 mg |
| Magnesium Stearate | 5.0 mg |

The finely ground active compound was mixed with the powdered excipients lactose, and magnesium stearate and packed into gelatin capsules.

| (F)-Tablet | |
| --- | --- |
| Ingredient | Amount per Tablet |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 3(D).

| (G)-Syrup | |
| --- | --- |
| Ingredient | Amount per 5 mL |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavour | q.s. |
| Glycerol | 500 mg |
| Sucrose | 2000 mg |
| Purified Water q.s. to | 5.0 mL |

A syrup containing other active ingredients in addition to a compound of formula (I) was prepared from the above ingredients by an analogous method to that described for Example 3(C) above.

| (H)-Nasal Spray | |
| --- | --- |
| Ingredient | Amount per 100.0 mL |
| Compound of Formula (I) | 1 g |
| Sodium Chloride | 0.8 g |
| Preservative | 0.5 g |
| Purified Water q.s. | 100.0 mL |

The preservative was dissolved in warm purified water and after cooling to 25°–30° C. the sodium chloride and the compound of formula (I) were added. The pH was then adjusted to 5.5–6.5 and purified water was added to bring the final volume to 100.0 mL.

| (I)-Ophthalmic Solution | |
| --- | --- |
| Ingredient | Amount per 100.0 mL |
| Compound of Formula (I) | 0.1 g |
| Sodium Chloride | 0.8 g |
| Preservative | 0.5 g |
| Water for Injection q.s. | 100.0 mL |

This formulation was prepared in a similar way to the nasal spray.

| (J)-Topical Cream | |
| --- | --- |
| Ingredient | Amount per 100.0 g |
| Compound of Formula (I) | 0.1 g |
| Emulsifying Wax, N.F. | 15.0 g |
| Mineral Oil | 5.0 g |
| White Petrolatum | 5.0 g |
| Preservative | 0.25 g |
| Purified Water q.s. | 100.0 g |

The preservative was dissolved in approximately 50 g of warm purified water and after cooling to about 25°–30° C. the compound of formula (I) was added. In a separate container the emulsifying wax, mineral oil and white petrolatum were mixed well and heated to approximately 70°–80° C. The aqueous solution containing the compound of formula (I) was added to the warm mixture of emulsifyng wax, mineral oil and petrolatum with vigorous mixing while cooling to 25° C. Additional purified water was added with mixing to bring the total weight of the cream to 100.0 g.

I claim:

1. A compound which is 2-[10-(2-Dimethylaminopropyl)-7-fluoro-2-phenothiazinyl]-2-methylpropionic acid or a salt, ester or amide thereof.

2. 2-[10-(2-Dimethylaminopropyl)-7-fluoro-2-phenothiazinyl]-2-methylpropionic acid or a pharmaceutically acceptable salt thereof.

3. The compound of claim 1 as the hydrochloride salt.

4. The compound of claim 1 as a sodium salt.

5. The compound of claim 1 as the ethyl ester.

6. A pharmaceutical composition comprising 2-[10-(2-Dimethylaminopropyl)-7-fluoro-2-phenothiazinyl]-2-methylpropionic acid or a pharmaceutically acceptable salt thereof together with a carrier therefor.

7. A method of relieving the detrimental effects of histamine in a mammal comprising administering to said mammal an effective amount of 2-[10-(2-Dimethylaminopropyl)-7-fluoro-2-phenothiazinyl]-2-methylpropionic acid or a salt, ester or amide thereof.

8. A method of claim 7 wherein the compound is administered as hydrochloride salt.

9. A method of claim 7 wherein the compound is administered as the sodium salt.

10. A methd of claim 7 wherein the compound is administered as the ethyl ester.

11. A method of claim 7 wherein the mammal is a human.

12. A method of claim 7 wherein the detrimental symptom is selected from the group comprising nasal allergy, perennial rhinitis, urticaria, antioneurotic oedema, allergic conjectivitis, food allergy, drug and serum reactions, insect bites and stings, desensitising reactions.

13. The method of claim 7 in which 2-[10-(2-dimethylaminopropyl)-7-fluoro-2-phenothiazinyl]-2-methylpropionic acid is administered.

14. The method of claim 7 in which a pharmaceutically acceptable salt of 2-[10(2-dimethylaminopropyl)-7-fluro-2-phenothiazinyl-2-methylpropionic acid is administered.

* * * * *